(12) United States Patent
Li et al.

(10) Patent No.: US 9,050,044 B2
(45) Date of Patent: Jun. 9, 2015

(54) PATHLENGTH ENHANCEMENT OF OPTICAL MEASUREMENT OF PHYSIOLOGICAL BLOOD PARAMETERS

(75) Inventors: Youzhi Li, Longmont, CO (US); Clark R. Baker, Jr., Newman, CA (US)

(73) Assignee: Covidien LP, Mansfield, MA (US)

( * ) Notice: Subject to any disclaimer, the term of this patent is extended or adjusted under 35 U.S.C. 154(b) by 246 days.

(21) Appl. No.: 13/494,630

(22) Filed: Jun. 12, 2012

(65) Prior Publication Data

US 2013/0331710 A1 Dec. 12, 2013

(51) Int. Cl.
A61B 5/02 (2006.01)
A61B 6/00 (2006.01)
A61B 5/1455 (2006.01)
A61B 5/00 (2006.01)

(52) U.S. Cl.
CPC ........... *A61B 5/14551* (2013.01); *A61B 5/6803* (2013.01)

(58) Field of Classification Search
CPC ........... A61B 5/14551; A61B 5/14553; A61B 2562/0242; A61B 5/6803; A61B 2562/0233; A61B 2562/043
USPC ................. 600/407, 473, 476, 310, 323, 328; 382/260
See application file for complete search history.

(56) References Cited

U.S. PATENT DOCUMENTS

| | | | |
|---|---|---|---|
| 5,413,100 A | 5/1995 | Barthelemy et al. | |
| 5,555,855 A | 9/1996 | Takahashi | |
| 6,058,324 A | 5/2000 | Chance | |
| 6,192,260 B1 | 2/2001 | Chance | |
| 6,246,892 B1 * | 6/2001 | Chance | 600/310 |
| 6,285,904 B1 * | 9/2001 | Weber et al. | 600/473 |
| 6,594,513 B1 * | 7/2003 | Jobsis et al. | 600/328 |
| 2004/0208390 A1 * | 10/2004 | Jiang et al. | 382/260 |
| 2006/0015021 A1 * | 1/2006 | Cheng | 600/310 |
| 2007/0088207 A1 * | 4/2007 | Mannheimer et al. | 600/323 |
| 2008/0139908 A1 | 6/2008 | Kurth | |
| 2010/0076319 A1 * | 3/2010 | Mannheimer et al. | 600/476 |
| 2011/0071373 A1 | 3/2011 | Li et al. | |

FOREIGN PATENT DOCUMENTS

| | | |
|---|---|---|
| RU | 2038037 | 6/1995 |
| RU | 2040912 | 8/1995 |

OTHER PUBLICATIONS

Vasilis Ntziachristos, et al.; "Oximetry Based on Diffuse Photon Density Wave Differentials;" Medical Physics; Feb. 2000; pp. 410-421; vol. 27, No. 2; Am. Assoc. Phys. Med.; Melville, NY, US.

* cited by examiner

*Primary Examiner* — Baisakhi Roy (57) ABSTRACT

Systems and methods for measuring a physiological parameter of tissue in a patient are provided herein. In a first example, a method of measuring a physiological parameter of blood in a patient is provided. The method includes emitting at least two optical signals for propagation through tissue of the patient, detecting the optical signals after propagation, identifying propagation pathlengths of the optical signals, and identifying detected intensities of the optical signals. The method also includes processing at least the propagation pathlengths to scale the detected intensities for determination of a value of the physiological parameter.

6 Claims, 4 Drawing Sheets

PATHLENGTH ENHANCEMENT OF OPTICAL MEASUREMENT OF PHYSIOLOGICAL BLOOD PARAMETERS

TECHNICAL FIELD

Aspects of the disclosure are related to the field of medical devices, and in particular, optical measurement of physiological parameters of blood and tissue.

TECHNICAL BACKGROUND

Various optical-based blood measurement devices, such as fingertip pulse oximetry devices, can measure some parameters of blood flow in a patient, such as heart rate and local oxygen saturation of hemoglobin. Other techniques can be employed for determination of regional saturation of hemoglobin, such as forehead-applied devices. These devices are non-invasive measurement devices, typically employing solid-state lighting elements, such as light-emitting diodes (LEDs) or solid state lasers, to introduce light into the tissue of a patient. The light is then detected and analyzed to determine the parameters of the blood flow in the patient.

However, conventional optical-based blood measurement devices typically are subject to patient-specific noise and inconsistencies which limits the accuracy of such devices. These patient-specific issues can include variations in tissue pigment, local blood flow or volume variations, vascular inhomogeneity of the tissue under measurement (i.e. a large vessel underneath device on tissue), tissue layer scattering, or tissue hydration, among others. Additionally, incorrect application of these devices can lead to incorrect determination of blood and tissue parameters due to optical shunting or undesired propagation of the optical signals through air gaps or blood-deficient tissue between optical emission and detection points.

OVERVIEW

Systems and methods for measuring a physiological parameter of tissue in a patient are provided herein. In a first example, a method of measuring a physiological parameter of blood in a patient is provided. The method includes emitting at least two optical signals for propagation through tissue of the patient, detecting the optical signals after propagation, identifying propagation pathlengths of the optical signals, and identifying detected intensities of the optical signals. The method also includes processing at least the propagation pathlengths to scale the detected intensities for determination of a value of the physiological parameter.

In another example, a method of operating a system for measuring a physiological parameter of blood in a patient is provided. The method includes emitting at least one optical signal for propagation into tissue of the patient via a tissue interface assembly, receiving the at least one optical signal after propagation, and identifying a propagation pathlength of the at least one optical signal. The method also includes processing at least the propagation pathlength to determine a state of the tissue interface assembly on the tissue.

In another example, a system for measuring a physiological parameter of blood in a patient is provided. The system includes a tissue interface assembly configured to emit at least one optical signal for propagation into tissue of the patient and receive the at least one optical signal after propagation. The system also includes a measurement system configured to identify a propagation pathlength of the at least one optical signal, and process at least the propagation pathlength to determine a state of the tissue interface assembly on the tissue.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views. While several embodiments are described in connection with these drawings, the disclosure is not limited to the embodiments disclosed herein. On the contrary, the intent is to cover all alternatives, modifications, and equivalents.

DETAILED DESCRIPTION

Various physiological parameters of tissue and blood of a patient can be determined non-invasively, such as optically. In one example, optical signals introduced into the tissue of the patient are modulated according to a high-frequency modulation signal to create a photon density wave (PDW) optical signal in the tissue undergoing measurement. In PDW techniques, an optical signal with a carrier wavelength is intensity modulated at a high frequency, on the order of 400-500 megahertz (MHz), although other frequencies are possible. Due to the interaction between the tissue or blood and the PDW optical signal, various characteristics of the PDW optical signal can be affected, such as through scattering or propagation by various components of the tissue and blood. The various physiological parameters can include any parameter associated with the blood or tissue of the patient, such as hemoglobin concentration (tHb), regional oxygen saturation (rSO2), arterial oxygen saturation (SpO2), heart rate, lipid concentrations, among other parameters, including combinations thereof.

Figure 1:
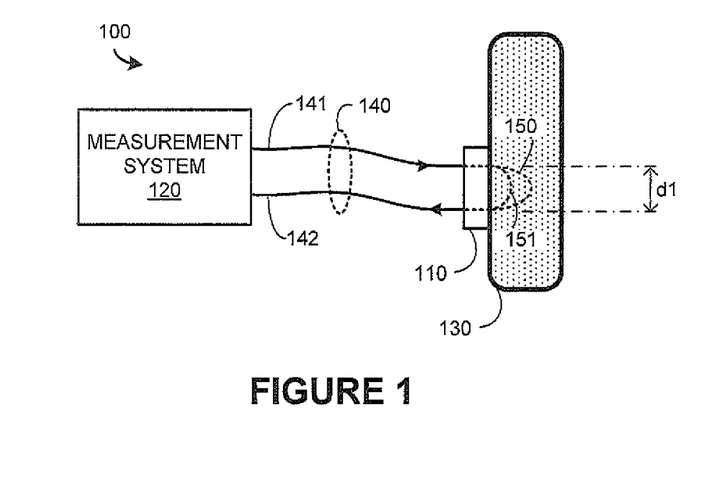
FIG. 1 is a system diagram illustrating a system for measuring a physiological parameter of blood in a patient.

As a first example of a system for applying optical signals to tissue of a patient, FIG. 1 is presented. FIG. 1 is a system diagram illustrating system 100 for measuring a physiological parameter of blood in a patient. FIG. 1 shows system 100 as including tissue interface assembly 110, measurement system 120, tissue 130, and signal link 140 which includes links 141-142. A representative view of the elements of system 100 is included in FIG. 1 to highlight these particular elements. It should be understood the features of FIG. 1 are merely intended to highlight various elements of system 100, and are not intended to be exact wireframe representations of the elements of system 100; variations are possible.

Signals generated by measurement system 120 are applied to tissue 130 for measurement of a physiological parameter, as indicated by optical signals 150-151. In this example, optical signals are transferred via optical link 141 to tissue interface assembly 110 for propagation in tissue 130. In other examples, link 141 is an electrical link and is configured to drive an optical emitter included within tissue interface assembly 110. Optical signals 150-151 are detected through tissue 130 and transferred to measurement system 120 over link 142. In this example, optical signals are transferred via optical link 142 to measurement system 120 for detection and processing. In other examples, a detector element is included in tissue interface assembly 110, and electrical signaling representative of the detected optical signals 150-151 are transferred over link 142. Optical link 141 is terminated at a first location of tissue interface assembly 110 and configured to emit optical signals 150-151 for propagation in tissue 130 at that first location. Likewise, optical link 142 is terminated at a second location of tissue interface assembly 110 and configured to receive optical signals 150-151 after propagation. Distance '111' of FIG. 1 indicates the distance between the first location and the second location. Example distances for d1 are 5 mm or 10 mm, although variations are possible.

In FIG. 1, optical signals 150-151 are introduced at a first location and received at a second location. Optical signals 150-151 are each shown to propagate along a different pathlength in tissue 130. The difference in pathlength can be caused by different properties of tissue 130 encountered by each optical signal or by different properties of optical signals 150-151. For example, when each of optical signals 150-151 comprises a different carrier wavelength, different propagation pathlengths through tissue 130 can occur. Different frequencies or wavelengths of optical signals can have different inherent absorption and propagation characteristics in blood and/or tissue. For example, red optical wavelengths typically do not traverse as much blood/tissue as infrared (IR) wavelengths since melanin in the tissue absorbs red better than IR. Thus, the propagation pathway for an IR wavelength signal may be longer than a red wavelength signal for the same distance d1. As a specific example, a red carrier wavelength is 660 nanometers and an IR carrier wavelength is 900 nanometers, although other carrier wavelengths are possible. In operation, measurement system 120 can process the different propagation pathlengths to scale detected intensities for each of optical signals 150-151 for determination of a value of a physiological parameter of tissue 130. It should be understood that the propagation pathlengths shown in FIG. 1 are merely representative of different propagations of the associated optical signals, and the pathlengths can comprise mean pathlengths.

Figure 2:
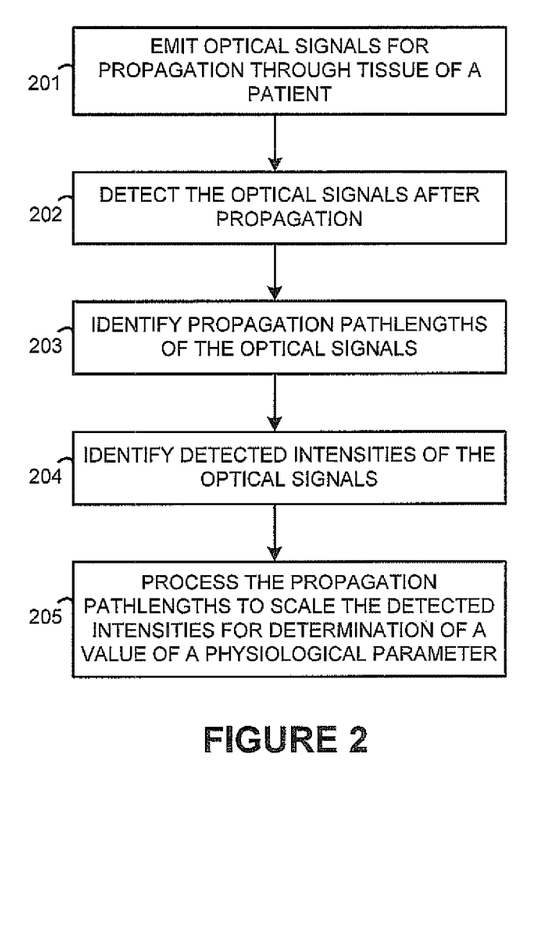
FIG. 2 is a flow diagram illustrating a method of operation of a system for measuring a physiological parameter of blood in a patient.

FIG. 2 is a flow diagram illustrating a method of operation of a system for measuring a physiological parameter of blood in a patient. Although the operations of FIG. 2 are discussed below as applied to system 100 found in FIG. 1, it should be understood that the operations of FIG. 2 can also be applied to system 300 of FIG. 3, system 500 of FIG. 5, or system 600 of FIG. 6, as well as other systems. The operations of FIG. 2 are referenced herein parenthetically.

In FIG. 2, tissue interface assembly 110 emits (201) optical signals for propagation through tissue of the patient. In the example shown in FIG. 1, measurement system 120 generates and transfers at least optical signals 150-151 over link 141 for propagation through tissue 130. These optical signals can include a single or multiple signals with a single or multiple carrier wavelengths. For example, both an infrared and visible based optical signal can be transferred over link 141. Tissue interface assembly 110 receives optical signals 150-151 and emits them for propagation through tissue 130. Optical interface elements, such as prisms, lenses, waveguides, and the like, can be included in tissue interface assembly 110 to couple optical signals 150-151 from link 141 to tissue 130. It should be noted that in alternate examples, electrical signals are transferred by measurement system 120 over link 141 and optical emitter elements in tissue interface assembly 110, such as solid state laser elements and the like, receive the electrical signals and emit optical signals 150-151 into tissue 130 responsive to the electrical signals.

Tissue interface assembly 110 detects (202) the optical signals after propagation. As shown in FIG. 1, optical signals 150-151 propagate through tissue 130, and are received by tissue interface assembly 110. These optical signals are both transferred over link 142 for receipt and processing by measurement system 120. Optical interface elements, such as prisms, lenses, waveguides, and the like, can be included in tissue interface assembly 110 to couple optical signals from tissue 130 to link 142. It should be noted that in alternate examples, optical detection elements in tissue interface assembly 110, such as photodetector elements and the like, receive optical signals 150-151 and transfer electrical signals over link 142 responsive to the optical signals.

Measurement system 120 identifies (203) propagation pathlengths of the optical signals. As shown in FIG. 1, optical signals 150-151 may each have different propagation properties through tissue 130, such as propagation pathlengths in tissue 130. After receiving the optical signals, or representations thereof, over link 142, measurement system 120 processes at least the optical signals to determine propagation pathlengths. In some examples, measurement system 120 processes phase delays or phase shifts of the optical signals to determine the propagation pathlengths. Other information can be processed to identify the propagation pathlengths, such as reference signals representing baseline phase delays for each optical signal, a carrier wavelength of each of the optical signals, propagation speeds or properties of tissue 130, or a separation distance between emission and detection points (such as 'd1'), among other information, including combinations and variations thereof. It should be understood that the propagation pathlengths shown in FIG. 1 are merely representative and can vary. FIG. 1 also shows tissue interface assembly 110 coupled to tissue 130 without gaps, and thus optical signals 150-151 are introduced into tissue 130. In other examples, such as those discussed in FIGS. 5-7, tissue interface assembly 110 may not properly mate or couple with tissue 130 and thus optical signals 150-151 may have different propagation pathlengths.

Measurement system 120 identifies (204) detected intensities of the optical signals. The intensities can be different for each of optical signals 150-151 due to the propagation through tissue 130, the properties of tissue 130 and components within tissue 130, such as blood, among others. After receiving the optical signals, or representations thereof, over link 142, measurement system 120 processes at least the optical signals to determine intensities after propagation through tissue 130. The intensities can be identified as brightness, luminosity, or signal strength and the like. In examples where detector elements are included in tissue interface assembly 110, the detector elements can convert the optical signals into electrical representations, and measurement system 120 can process the electrical representations to determine the intensities.

Measurement system 120 processes (205) at least the propagation pathlengths to scale the detected intensities for determination of a value of a physiological parameter. Each optical signal 150-151 can have different propagation properties such as a propagation pathlength. These differences in propagation pathlength can lead to inaccuracies and errors in the calculation and processing of the optical signal intensities or other properties to identify values of physiological parameters. Therefore, measured properties of the optical signals, such as intensity, are scaled according to the associated propagation pathlengths of the optical signals and the scaled values are used in determination of the value of the physiological parameter. As noted herein, the physiological parameter can include any parameter associated with the blood or tissue of the patient, such as hemoglobin concentration (tHb), regional oxygen saturation (rSO2), arterial oxygen saturation (SpO2), heart rate, lipid concentrations, among other parameters, including combinations thereof.

In a specific example, such as when optical signals with multiple carrier wavelengths are employed, a ratiometric relationship is employed between detected intensities of at least two optical signals to determine a value of a physiological parameter. Propagation pathlength variations encountered during propagation of the optical signals can disturb these ratiometric relationships. Pathlength variations can be caused by different propagation pathlengths in tissue for different carrier wavelengths, invalid or improper sensor application on tissue, or insufficiently perfused tissue under measurement, among other causes. Thus, the propagation pathlengths of the optical signals can be used to scale the ratiometric relationships to compensate for different propagation pathlengths and reduce errors and inconsistencies in determinations of values of physiological parameters.

Figure 3:
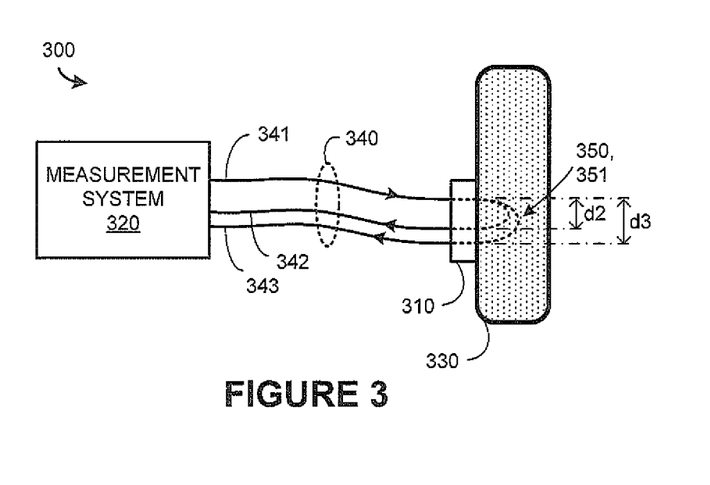
FIG. 3 is a system diagram illustrating a system for measuring a physiological parameter of blood in a patient.

FIG. 3 is presented as a second example of a system for applying optical signals to tissue of a patient. FIG. 3 is a system diagram illustrating system 300 for measuring a physiological parameter of blood in a patient. System 300 can be an alternate configuration for system 100, although other configurations can be employed. FIG. 3 shows system 300 as including tissue interface assembly 310, measurement system 320, tissue 330, and signal link 340 which includes links 341-343. A representative view of the elements of system 300 is included in FIG. 3 to highlight these particular elements. It should be understood the features of FIG. 3 are merely intended to highlight various elements of system 300, and are not intended to be exact wireframe representations of the elements of system 300; variations are possible.

Signals generated by measurement system 320 are applied to tissue 330 for measurement of a physiological parameter, as indicated by optical signals 350-351. In this example, optical signals are transferred via optical link 341 to tissue interface assembly 310 for propagation in tissue 330. In other examples, link 341 is an electrical link and is configured to drive an optical emitter (or emitters) included within tissue interface assembly 310. Optical signals 350-351 are detected through tissue 330 and transferred to measurement system 320 over both link 342 and link 343. In this example, optical signals are transferred via optical links 342-343 to measurement system 320 for detection and processing. In other examples, a detector element (or elements) is included in tissue interface assembly 310, and electrical signaling representative of the detected optical signals 350-351 are transferred over links 342-343.

Optical link 341 is terminated at a first location in tissue interface assembly 310 and configured to emit optical signals 350-351 for propagation in tissue 330 at that first location. Optical link 342 is terminated at a second location in tissue interface assembly 310 and configured to receive optical signals 350-351 after propagation. Optical link 343 is terminated at a third location in tissue interface assembly 310 and configured to receive optical signals 350-351 after propagation. Distance 'd2' of FIG. 3 indicates the distance between the first location and the second location, and distance 'd3' of FIG. 3 indicates the distance between the first location and the third location. Example distances include 5 mm for d2 and 10 mm for d3, although variations are possible. Thus, optical signals 350-351 are each introduced at a first location and both are received at a second location associated with link 342 and a third location associated with link 343.

Optical signals 350-351 in FIG. 3 include optical signals of at least two carrier wavelengths, and a portion of each optical signal is received at each detection point shown. Optical signals 350-351 can also each propagate along a different pathlength in tissue 330. The difference in pathlength can be caused by different properties of tissue 330 encountered by each optical signal, the different detection distances d2 and d3, or by different properties of optical signals 350-351, such as those discussed above for FIG. 1, including combinations thereof. Additionally, a portion of each of optical signals 350-351 is transferred over each optical link 342-343. In operation, measurement system 320 can process the different propagation pathlengths to scale detected intensities for each of optical signals 350-351 for determination of a value of a physiological parameter of tissue 330. It should be understood that the propagation pathlengths shown in FIG. 3 are merely representative of different propagations of the associated optical signals, and the pathlengths can comprise mean pathlengths.

Figure 4:
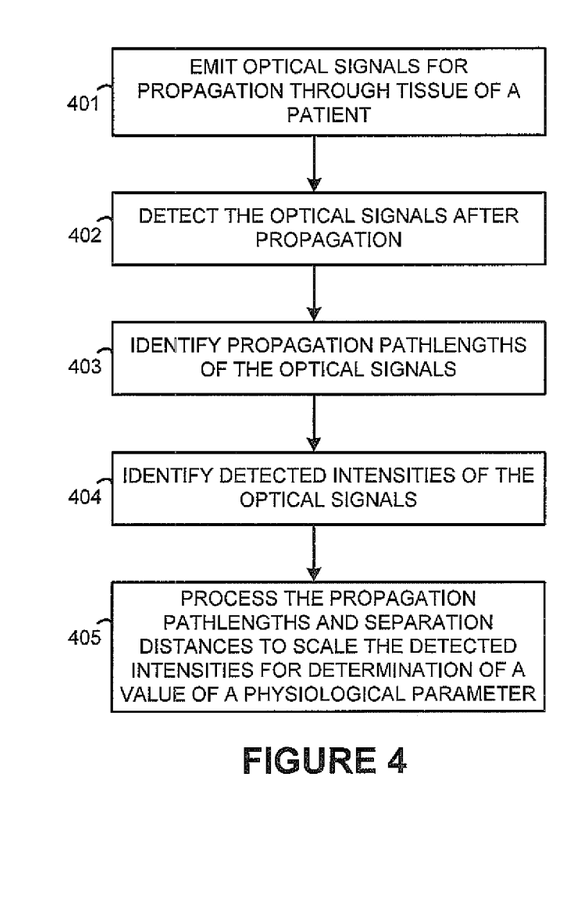
FIG. 4 is a flow diagram illustrating a method of operation of a system for measuring a physiological parameter of blood in a patient.

FIG. 4 is a flow diagram illustrating a method of operation of a system for measuring a physiological parameter of blood in a patient. Although the operations of FIG. 4 are discussed below as applied to system 300 found in FIG. 3, it should be understood that the operations of FIG. 4 can also be applied to system 100 of FIG. 1, system 500 of FIG. 5, or system 600 of FIG. 6, as well as other systems. The operations of FIG. 4 are referenced herein parenthetically.

In FIG. 4, tissue interface assembly 310 emits (401) optical signals for propagation through tissue of the patient. In the example shown in FIG. 3, measurement system 320 generates and transfers at least optical signals 350-351 over link 341 for propagation through tissue 330. In this example, optical signals 350-351 can comprise infrared and visible optical components which are both transferred over link 341. Tissue interface assembly 310 receives optical signals 350-351 and emits them for propagation through tissue 330. Optical interface elements, such as prisms, lenses, waveguides, and the like, can be included in tissue interface assembly 310 to couple optical signals 350-351 from link 341 to tissue 330. It should be noted that in alternate examples, electrical signals are transferred by measurement system 320 over link 341 and optical emitter elements in tissue interface assembly 310, such as solid state laser elements and the like, receive the electrical signals and emit optical signals 350-351 into tissue 330 responsive to the electrical signals.

Tissue interface assembly 310 detects (402) the optical signals after propagation. As shown in FIG. 3, optical signals 350-351 propagate through tissue 330, and are received by tissue interface assembly 310. A first portion of optical signals 350-351 is received by tissue interface assembly 310 for transfer over link 342 and a second portion of optical signals 350-351 is received by tissue interface assembly 310 for transfer over link 343. These optical signals are transferred over the respective links 342-343 for receipt and processing by measurement system 320. Optical interface elements, such as prisms, lenses, waveguides, and the like, can be included in tissue interface assembly 310 to couple optical signals from tissue 330 to links 342-343. It should be noted that in alternate examples, optical detection elements in tissue interface assembly 310, such as photodetector elements and the like, receive optical signals 350-351 and transfer electrical signals over links 342-343 responsive to the optical signals.

Measurement system 320 identifies (403) propagation pathlengths of the optical signals. As shown in FIG. 3, optical signals 350-351 each have different propagation properties through tissue 330, such as propagation pathlengths in tissue 330. Also, portions of optical signals 350-351 are detected at different detection distances from the input point, namely d2 and d3. After receiving the optical signals, or representations thereof, over links 342-343, measurement system 320 processes at least the optical signals and separation distances d2 and d3 to determine propagation pathlengths. In some examples, measurement system 320 processes phase delays or phase shifts of the optical signals to determine the propagation pathlengths.

FIG. 3 shows a first portion of optical signals 350-351 received at distance d2, and a second portion of optical signals 350-351 received at distance d3. A first set of propagation pathlengths for signal components of the different carrier wavelengths of optical signals 350-351 can be determined for the first portion received at the first distance d2, and a second set of propagation pathlengths for signal components of the different carrier wavelengths of optical signals 350-351 can be determined for the second portion received at the second distance d3. In examples with two carrier wavelengths, such as visible and infrared, four total propagation pathlengths can be determined. Specifically, a propagation pathlength can be determined for each of the visible and infrared signal portions received at distance d2, and a propagation pathlength can be determined for each of the visible and infrared signal portions received at distance d3. It should be understood that other carrier wavelengths or frequencies can be employed.

Other information can be processed to identify the propagation pathlengths, such as reference signals representing baseline phase delays for each optical signal, a carrier wavelength of each of the optical signals, or propagation speeds through tissue 330, or properties of tissue 330, among other information, including combinations and variations thereof. It should be understood that the propagation pathlengths shown in FIG. 3 are merely representative in and can vary. FIG. 3 also shows tissue interface assembly 310 coupled to tissue 330 without gaps, and thus optical signals 350-351 are introduced into tissue 330. In other examples, such as those discussed in FIGS. 5-7, tissue interface assembly 310 may not properly mate or couple with tissue 330 and thus optical signals 350-351 may have different propagation pathlengths.

Measurement system 320 identifies (404) detected intensities of the optical signals. The intensities can be different for each of optical signals 350-351 due to the propagation through tissue 330, distances d2 and d3, the properties of tissue 330, and components within tissue 330, such as blood, among others. After receiving the optical signals, or representations thereof, over links 342-343, measurement system 320 processes at least the optical signals to determine intensities after propagation through tissue 330. The intensities can be identified as brightness, luminosity, or signal strength and the like. In examples where detector elements are included in tissue interface assembly 310, the detector elements can convert the optical signals into electrical representations, and measurement system 320 can process the electrical representations to determine the intensities.

Measurement system 320 processes (405) at least the propagation pathlengths and the separation distances to scale the detected intensities for determination of a value of a physiological parameter. As discussed above, each of optical signals 350-351 can have different propagation properties such as a propagation pathlength. These differences in propagation pathlength can lead to inaccuracies and errors in the calculation and processing of the optical signal intensities or other properties to identify values of physiological parameters.

Different carrier wavelengths of optical signals 350-351 can propagate differently through tissue 330 due to the influence of absorbent or reflectance differences of components of tissue 330 for different wavelengths, different propagation speeds in tissue 330 for different wavelengths, or other wavelength-dependent propagation properties, and thus may penetrate to different depths in tissue 330 or traverse different propagation paths in tissue 330. Therefore, measured properties of the optical signals, such as intensity, are scaled according to the associated propagation pathlengths of the optical signals and the scaled values are used in determination of the value of the physiological parameter. Also, since optical signals 350-351 are received at two distances, namely distances d2 and d3, the propagation pathways determined for each distance can be employed to scale the intensities for the optical signals received at each detection distance. In some examples, processing at least the propagation pathlengths to scale the detected intensities comprises processing a first carrier wavelength of a first optical signal and a second carrier wavelength of a second optical signal, distances between a first emission location and each of a second receive location and a third receive location, and the propagation pathlengths of the first optical signal and the second optical signal to scale the detected intensities of the first optical signal and the second optical signal.

In some examples, a ratio of intensities of two carrier wavelength portions of the optical signals are scaled by a ratio of associated propagation pathlengths for the optical signals associated with the two carrier wavelength portions. As noted herein, the physiological parameter can include any parameter associated with the blood or tissue of the patient, such as hemoglobin concentration (tHb), regional oxygen saturation (rSO2), arterial oxygen saturation (SpO2), heart rate, lipid concentrations, among other parameters, including combinations thereof.

Referring back to FIGS. 1 and 3, tissue interface assembly 110 and tissue interface 330 each can comprise a physical structure having a surface that couples to biological tissue, namely tissue 130 or 330. Tissue interface assembly 110 includes a mechanical configuration to position and hold optical links 141-142 in a desired arrangement relative to tissue 130. Tissue interface assembly 310 can include similar configurations for optical links 341-343. These configurations can include elements such as grooves, channels, holes, snap-fit features, or other elements to route optical fibers or optical links to a desired position in the tissue interface assembly. Tissue interface assemblies 110 or 330 may each be comprised of plastic, foam, rubber, glass, metal, adhesive, or some other material, including combinations thereof. Typically, the materials selected for tissue interface assemblies 110 and 330 each include biocompatible materials. Specifically, biocompatible materials are inert, non-toxic and hypoallergenic, and typically exclude latex and heavy metals, for example. Also, the materials selected for tissue interface assemblies 110 and 310 are each typically selected to avoid materials that are difficult to clean. In some examples, tissue interface assemblies 110 and 330 are each comprised of optically transmissive materials, such as optically transmissive plastic, glass, acrylic glass, PMMA, or other materials, including combinations thereof. Optically transmissive adhesives can also be employed in each of tissue interface assemblies 110 and 330, such as to mate optical fibers to optical interface elements of the tissue interface assembly. These optical adhesives can comprise compositions which are cured using ultraviolet (UV) light. Other optically transmissive adhesives can be employed, including combinations thereof. Various optical interfacing elements can be employed to optically couple optical signals carried by optical fibers to the tissue, such as prisms, reflective surfaces, refractive materials, or the like.

Tissue 130 and 330 are each shown as a bulk tissue of a patient. It should be understood that the tissue can be any tissue portion of a patient, such as a finger, toe, arm, leg, earlobe, torso, forehead, or other tissue portion of a patient. In this example, the tissue is a portion of the tissue of a patient undergoing measurement of a physiological blood parameter. The wavelength of signals applied to the tissue can be selected based on many factors, such as optimized to a wavelength strongly absorbed by hemoglobin, lipids, proteins, or other tissue and blood components of the tissue.

Measurement systems 120 and 320 can each include optical interfaces, digital processors, computer systems, microprocessors, circuitry, non-transient computer-readable media, user interfaces, or other processing devices or software systems, and may be distributed among multiple processing devices. Measurement systems 120 and 320 can also each include photon density wave (PDW) generation and measurement equipment, electrical to optical conversion circuitry and equipment, optical modulation equipment, and optical waveguide interface equipment. Measurement systems 120 and 320 can also each include optical emitter elements such as lasers, laser diodes, solid-state lasers, light-emitting diodes (LEDs), or other optical emitter devices, along with associated driving circuitry. Measurement systems 120 and 340 can also each include optical detector elements, such as a photodiode, phototransistor, avalanche photodiode (APD), photomultiplier tube, charge coupled device (CCD), or other optoelectronic sensor, along with associated receiver circuitry such as amplifiers or filters. Optical couplers, adhesives, cabling, or attachments can be included to optically mate emitter or detector elements to optical fibers.

Optical links 141-142 and 341-343 each comprise an optical waveguide, such as an optical fiber, and each use glass, polymer, air, space, or some other material as the transport media for transmission of light, and can each include multimode fiber (MMF) or single mode fiber (SMF) materials. A sheath or loom can be employed to bundle associated optical links 141-142 and 341-343 together or with further optical links for convenience, as indicated by links 140 and 340. One end of each of optical links 141-142 and 341-343 mates with an associated optical driver or detector component of measurement system 120 or 320, and an end of each of optical links 141-142 and 341-343 is configured to terminate in a tissue interface assembly for optically interfacing with tissue. Each of optical links 141-142 and 341-343 may include many different signals sharing the same associated link, as represented by the associated lines in FIGS. 1 and 3, comprising channels, forward links, reverse links, frequencies, wavelengths, modulation frequencies, carriers, timeslots, spreading codes, logical transportation links, or communication directions.

Also, although FIGS. 1 and 3 each illustrate optical links 141-142 and 341-343, it should be understood that any number of input links and output links can be included, as well as any associated optical source and detector equipment. For example, a tissue interface assembly may route many optical fibers to different physical locations on the tissue, and these optical fibers can carry optical signals of different wavelengths. Alternatively, or in addition, a tissue interface assembly may have measurement links positioned at different distances from input links or positioned over different anatomical structures. Also, although FIGS. 1 and 3 are each shown as carrying optical signals, in further examples a direct optical source can be included in the tissue interface assembly and applied to the tissue. Such direct light sources can include light-emitting diodes (LEDs), laser sources, solid state laser diodes, or other signal sources, including combinations thereof.

The term 'optical' or 'light' is used herein for convenience. It should be understood that the applied and detected signals are not limited to visible light, and can comprise any photonic, electromagnetic, or energy signals, such as visible, infrared, near-infrared, ultraviolet, radio, x-ray, gamma, or other signals. Additionally, the use of optical fibers or optical cables herein is merely representative of a waveguide used for propagating signals between a transceiver and tissue of a patient. Suitable waveguides would be employed for different electromagnetic signal types.

Figure 5:
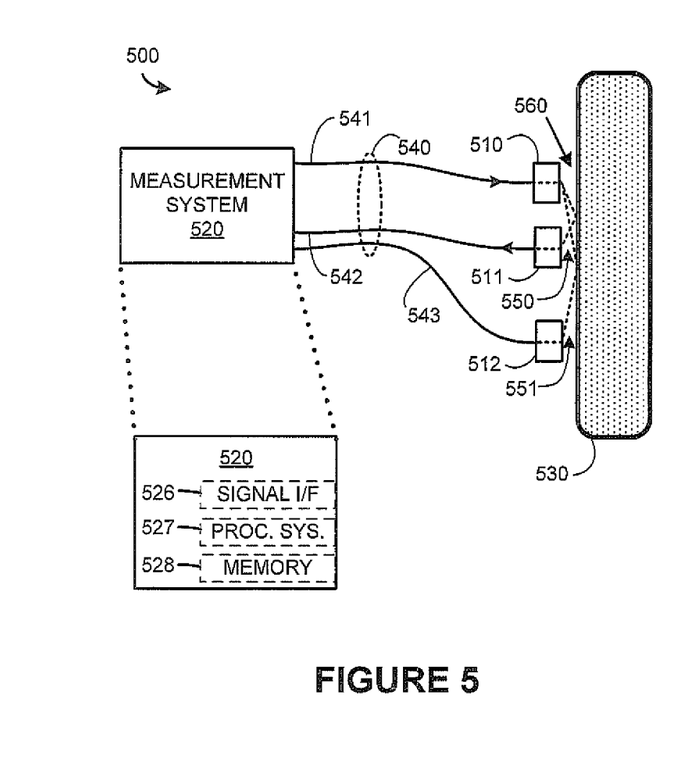
FIG. 5 is a system diagram illustrating a system for measuring a physiological parameter of blood in a patient.
Figure 6:
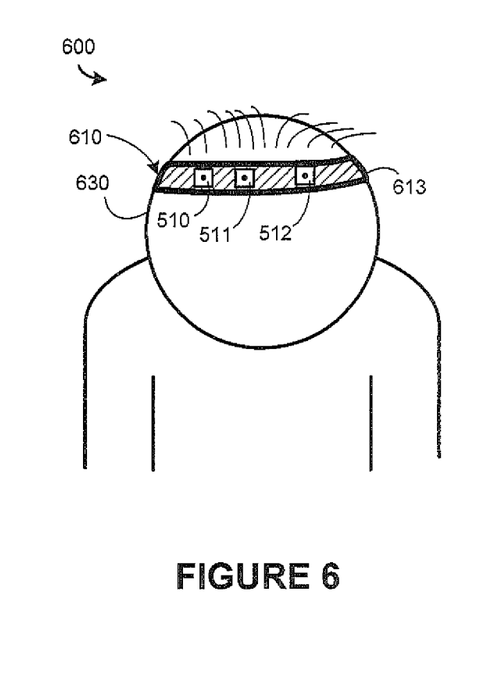
FIG. 6 is a system diagram illustrating a measurement environment for measuring a physiological parameter of blood in a patient.
Figure 7:
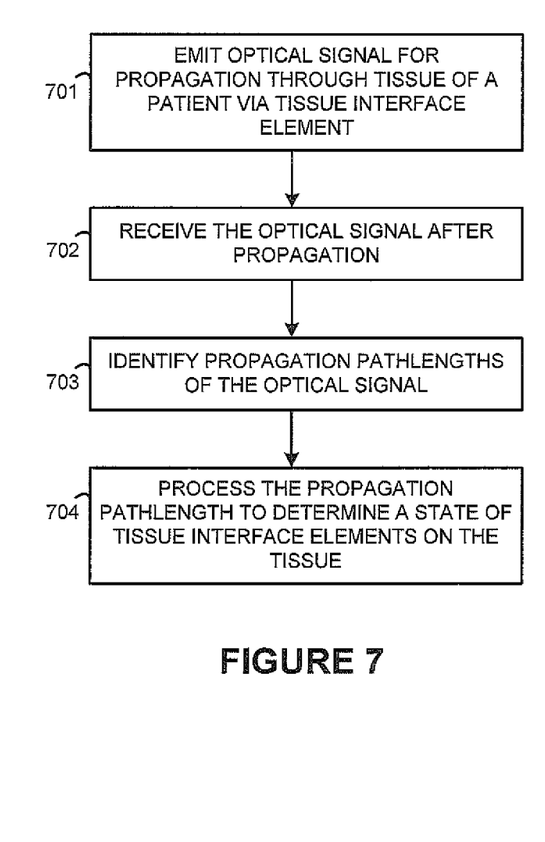
FIG. 7 is a flow diagram illustrating a method of operating a system for measuring a physiological parameter of blood in a patient.

FIGS. 5 and 6 include further examples of systems for measuring a physiological parameter of blood in a patient, and FIG. 7 includes an example method of operation of system 500 of FIG. 5 or system 600 of FIG. 6. The elements of FIGS. 5 and 6 can include elements similar to those found in FIGS. 1 and 3, although other configurations are possible. FIG. 5 illustrates a system 500 for measuring regional oxygen saturation of blood in tissue, while FIG. 6 illustrates an example of system 500 employed on a forehead portion of a patent to measure regional oxygen saturation of blood in the patient.

Regional oxygen saturation measurement typically includes steady state or "DC" measurement techniques, where pulsatile perturbation of tissue by vascular activity is not significant. Also, longer distances are employed in regional oxygen saturation measurement, such as 10 millimeters (mm) and 40 mm from an optical signal input point to detection points. Also, a lower frequency of modulation of any associated optical signals is typically employed, such as 50-100 megahertz (MHz) versus 400-500 MHz for photon-density wave (PDW) techniques. Although FIGS. 5-7 discuss regional oxygen saturation measurement, the systems and techniques can be applied to other measurements such as the PDW techniques described above in FIGS. 1-4.

FIG. 5 includes system 500 which includes tissue interface elements 510-512, measurement system 520, tissue 530, and optical link 540. A representative view of the elements of system 500 is included in FIG. 5 to highlight these particular elements. It should be understood the features of FIG. 5 are merely intended to highlight various elements of system 500, and are not intended to be exact wireframe representations of the elements of system 500; variations are possible.

Signals generated by measurement system 520 are emitted for propagation into tissue 530 for measurement of a physiological parameter, as indicated by optical signals 550-551. In this example, optical signals are transferred via optical fiber 541 to tissue interface element 510 for propagation into tissue 530. In other examples, optical fiber 541 is instead an electrical link and is configured to drive an optical emitter included within tissue interface element 510. Optical signals 550-551 are received after propagation and transferred to measurement system 520 over associated optical fiber 542-543. In this example, optical signals are transferred via optical fibers 542-542 to measurement system 520 for detection and processing. In other examples, detector elements are included in tissue interface elements 511-512, and electrical signaling representative of the detected optical signals 550-551 are instead transferred over associated link 542-543. Optical fiber 541 is terminated in tissue interface element 510 and configured to emit optical signals 550-551 for propagation into tissue 530 from tissue interface element 510. Likewise, optical fiber 542 is terminated in tissue interface element 511 and configured to receive optical signal 550 after propagation, and optical fiber 543 is terminate in tissue interface element 512 and configured to receive optical signal 551 after propagation.

In FIG. 5, optical signals 550-551 are both introduced at a first location and each are received at different locations. Optical signals 550-551 are each shown to propagate a different pathlength before receipt. As shown in FIG. 5, tissue interface elements 511-512 are not coupled to tissue 530, and instead each has gap 560 between tissue 530 and the associated tissue interface element. Thus, the majority of optical energy associated with optical signals 550-551 travels through gap 560, such as air or space, between tissue interface elements 510-512 and does not propagate into tissue 530 as intended. It should be understood that the propagation pathlengths shown in FIG. 5 are merely representative of different propagations of the associated optical signals, and the pathlengths can comprise mean pathlengths.

FIG. 5 also shows a detailed representation of measurement system 520. Measurement system 120 of FIG. 1 or measurement system 320 of FIG. 3 can include elements similar to measurement system 520, although other configurations are possible. Likewise, measurement system 520 can include equipment and systems as discussed herein for measurement system 120 and measurement system 320, although variations are possible. Measurement system 520 comprises signal interface 526, processing system 527, and memory 528.

In operation, processing system 527 is operatively linked to signal interface 526 and memory 527. Processing system 527 is capable of executing software stored in memory 527. When executing the software, processing system 527 drives measurement system 520 to operate as described herein. Measurement system 520 can also include a user interface, such as user input devices and a display for monitoring, altering, or controlling a status or configuration of measurement system 520.

Processing system 527 may be implemented within a single processing device but may also be distributed across multiple processing devices or sub-systems that cooperate in executing program instructions. Examples of processing system 527 include general purpose central processing units, microprocessors, application specific processors, and logic devices, as well as any other type of processing device.

Signal interface 526 includes optical interfaces for coupling optical signals generated by measurement system 520 to optical fiber 541 as well as for coupling optical signals received by tissue interface elements over optical fibers 542-543. Examples of signal interface 526 include optical couplers, optical emitters and detector sensors and circuitry, optical connectors, transceivers, or other optical interfacing elements. In examples where measurement system 520 instead transfers or receives electrical signals to/from a tissue interface element or assembly instead of optical signals, associated electrical interfaces can be included in signal interface 526, such as transceivers, RF couplers, filters, electrical connectors, or other electrical interfacing equipment.

Memory 528 may comprise any storage media readable by processing system 527 and capable of storing software. Memory 528 may include volatile and nonvolatile, removable and non-removable media implemented in any method or technology for storage of information, such as computer readable instructions, data structures, program modules, or other data. Memory 528 may be implemented as a single storage device but may also be implemented across multiple storage devices or sub-systems. Memory 528 may comprise additional elements, such as a controller, capable of communicating with processing system 527. Examples of storage media include random access memory, read only memory, and flash memory, as well as any combination or variation thereof, or any other type of storage media. In some implementations, the storage media may be a non-transitory storage media. In some implementations, at least a portion of the storage media may be transitory. It should be understood that in no case is the storage media a propagated signal.

Software stored on or in memory 528 may comprise computer program instructions, firmware, or some other form of machine-readable processing instructions having processes that when executed by processing system 527 direct measurement system 520 to operate as described herein. For example, software drives measurement system 520 to generate and transfer optical signals for propagation into tissue, receive optical signals after propagation, determine propagation pathlengths of the optical signals, determine values of physiological parameters, and identify states of a tissue interface assemblies or elements, among other operations. The software may also include user software applications. The software may be implemented as a single application or as multiple applications. In general, the software may, when loaded into processing system 527 and executed, transform processing system 527 from a general-purpose device into a special-purpose device customized as described herein.

FIG. 6 illustrates system 600 as an example of system 500 employed on a forehead portion of a patent. Specifically, system 600 includes headband 610, tissue interface assembly 613, and patient 630. Tissue interface assembly 613 includes tissue interface elements 510-512 from system 500. Patient 630 is included as an example of tissue 530, and is merely representative of a patient undergoing measurement, variations are possible. Headband 610 comprises a band which is configured to fit around the head of a patient, and may be composed of fabric, fasteners, adhesive materials, flexible materials, or other elements to couple elements 510-512 to the forehead of patient 630. In some examples, headband 610 is omitted and elements 510-512 are coupled to patient 630 by adhesive materials. Alternately, headband 610 could instead be a finger clamp, wrist band, leg band, or other patient interface element. Associated cabling, links, and measurement systems are omitted from FIG. 6 for clarity.

As shown in FIG. 6, tissue interface elements 510-512 are spaced apart. Example distances can include 10 millimeters for a distance between element 510 and element 511, and 40 millimeters for a distance between element 510 and element 512. Other spacing or separation distances are possible.

FIG. 7 is a flow diagram illustrating a method of operating a system for measuring a physiological parameter of blood in a patient. Although the operations of FIG. 7 are discussed below as applied to system 500 in FIG. 5 or system 600 in FIG. 6, it should be understood that the operations of FIG. 7 can also be applied to system 100 of FIG. 1, system 300 of FIG. 3, as well as other systems. Also, although the operations of FIG. 7 discuss tissue interface elements 510-512 of FIG. 5, it should be understood that tissue interface assembly 613 and headband 610 of FIG. 6 can instead be employed. The operations of FIG. 7 are referenced herein parenthetically.

In FIG. 7, tissue interface element 510 emits (701) optical signals for propagation through tissue of the patient. In the example shown in FIG. 5, measurement system 520 generates and transfers at least optical signals 550-551 over link 541 for propagation through tissue 530. These optical signals can include a single or multiple signals with a single or multiple carrier frequencies. For example, both an infrared and visible optical signal can be transferred over link 541. Tissue interface element 510 receives optical signals 550-551 over link 541 and emits the optical signals for propagation through tissue 530. Optical interface elements, such as prisms, lenses, waveguides, and the like, can be included in tissue interface element 510 to couple optical signals 550-551 from link 541 to tissue 530. It should be noted that in alternate examples, electrical signals are transferred by measurement system 520 over link 541 and optical emitter elements in tissue interface element 510, such as solid state laser elements and the like, receive the electrical signals and emit optical signals 550-551 for propagation into tissue 530 responsive to the electrical signals.

Tissue interface elements 511-512 each receive (702) the optical signals after propagation. As shown in FIG. 5, optical signals 550-551 do not significantly propagate into tissue 530 and are received by tissue interface elements 511-512 via propagation across the surface of tissue 530 and through gap 560 by reflection and direct transmission. These received optical signals are transferred over associated links 542-543 for receipt and processing by measurement system 520. Optical interface elements, such as prisms, lenses, waveguides, and the like, can be included in tissue interface elements 511-512 to couple received optical signals to associated links 542-543. It should be noted that in alternate examples, optical detection elements in tissue interface elements 511-512, such as photodetector elements and the like, receive optical signals 550-551 and transfer electrical signals over associated links 542-543 responsive to the optical signals.

Measurement system 520 identifies (703) a propagation pathlength of at least one optical signal. As shown in FIG. 5, optical signals 550-551 may each have different propagation properties through gap 560, such as propagation pathlengths through gap 560. After receiving an optical signal, or representation thereof, over any of links 542-543, measurement system 520 processes at least one optical signal to determine a propagation pathlength.

In some examples, measurement system 520 processes a phase delay or phase shift of an optical signal to determine the propagation pathlength. The phase delay or phase shift can be in relation to a reference signal, or to a version of the associated optical signal that does not propagate from tissue interface element 510, such as an optical signal internally shunted in measurement system 520. In further examples, a reference measurement signal is included in link 540 which receives optical signals from link 541 within or near tissue interface element 510 without significant propagation external to the tissue interface element (system 500 can include a further reference optical link in such examples).

Other information can be processed to identify the propagation pathlengths, such as a reference signal internal to measurement system 520 representing baseline phase for an optical signal, a carrier wavelength of the optical signal, a propagation speed of the optical signal in tissue, properties of tissue 530, or a separation distance between emission and detection points, among other information, including combinations and variations thereof. It should be understood that the propagation pathlengths shown in FIG. 5 are merely representative and can vary. FIG. 5 also shows gap 560 between tissue interface elements 510-511 and tissue 530, different gap sizes and configurations are possible. In further examples, tissue interface elements 510-511, or ones thereof, are coupled to tissue 530 without gaps, and thus optical signals 550-551 are introduced into tissue 530.

Measurement system 520 processes (704) at least one propagation pathlength to determine a state of tissue interface elements 510-512 on tissue 530. In some examples, processing at least one propagation pathlength of an optical signal to determine the state of the tissue interface elements on the tissue includes comparing the propagation pathlength of the optical signal to a pathlength range to determine an invalid application of the tissue interface element. Improper or invalid tissue interface element applications to tissue include shunting of optical signals between emission and detection elements without significant penetration or propagation into tissue 530. Other tissue applications can include variations in tissue pigmentation, variations in local blood flow or volume, vascular inhomogeneities (such as large vessel underneath tissue interface elements), tissue layer scattering, or tissue hydration variations, including combinations and variations thereof. The pathlength range can be an expected range of a propagation pathlength for an optical signal properly introduced into tissue 530 and after propagation through tissue 530. The range can include a first threshold propagation pathlength indicating a minimum propagation pathlength and a second threshold propagation pathlength including a maximum propagation pathlength. If the detected propagation pathlength does not meet the first or second thresholds, then the optical signal is determined to have propagated an undesired or invalid path, such as through gap 560, through insufficiently perfused tissue, or other paths other than the desired path through sufficiently perfused tissue 530.

In another example, processing at least the propagation pathlength to determine the state of the tissue interface elements on the tissue comprises determining the state of the tissue interface assembly as including gap 560 between the tissue interface element 510 introducing the optical signals and tissue 530. In yet another example, processing at least the propagation pathlength to determine the state of the tissue interface elements on the tissue comprises determining the state of at least one of tissue interface elements 511-512 as including gap 560 between the associated tissue interface element detecting or receiving the optical signal and tissue 530. In yet further examples, an invalid application of the tissue interface elements 510-512 comprises an application of ones of tissue interface elements onto tissue perfused by blood below a perfusion threshold.

If the state of tissue interface elements 510-512 on tissue 530 indicates a proper application of the tissue interface elements, then measurement system 520 can process a propagation pathlength of at least one detected optical signal and a detected intensity of the at least one optical signal to determine of a value of the physiological parameter. As noted herein, the physiological parameter can include any parameter associated with the blood or tissue of the patient, such as hemoglobin concentration (tHb), regional oxygen saturation (rSO2), arterial oxygen saturation (SpO2), heart rate, lipid concentrations, among other parameters, including combinations thereof.

The included descriptions and figures depict specific embodiments to teach those skilled in the art how to make and use the best mode. For the purpose of teaching inventive principles, some conventional aspects have been simplified or omitted. Those skilled in the art will appreciate variations from these embodiments that fall within the scope of the invention. Those skilled in the art will also appreciate that the features described above can be combined in various ways to form multiple embodiments. As a result, the invention is not limited to the specific embodiments described above, but only by the claims and their equivalents.

What is claimed is:

1. A method of measuring a physiological parameter of blood in a patient, the method comprising:
    emitting at least two optical signals for propagation through tissue of the patient using a tissue interface positioned at an emission location of the tissue, the at least two optical signals carried over a common optical fiber and emitted by the tissue interface at the emission location;
    detecting the optical signals after propagation at two or more different detection locations of the tissue separate from the emission location, each different detection location corresponding to one of the at least two optical signals;
    identifying propagation pathlengths of the optical signals based at least on propagation differences among the optical signals between the emission location and the detection locations;
    detecting presence of a gap between the tissue interface and the tissue based at least on a propagation pathlength of one of the optical signals;
    identifying detected intensities of the optical signals; and
    when the presence of the gap is not detected, processing at least the propagation pathlengths to scale the detected intensities in determination of a value of the physiological parameter.

2. The method of claim 1, wherein emitting the at least two optical signals comprises emitting a first optical signal and a second optical signal at the emission location of the tissue;
    wherein detecting the optical signals after propagation comprises detecting the first optical signal at a first detection location of the tissue and detecting the second optical signal at a second detection location of the tissue different than the first detection location;
    wherein processing at least the propagation pathlengths to scale the detected intensities comprises processing a first carrier wavelength of the first optical signal and a second carrier wavelength of the second optical signal, distances between the emission location and each of the first detection location and the second detection location, and the propagation pathlengths of the first optical signal and the second optical signal to scale the detected intensities.

3. The method of claim 1, wherein processing at least the propagation pathlengths to scale the detected intensities comprises scaling a ratio of the intensities of the at least two optical signals with a ratio of the propagation pathlengths of the at least two optical signals.

4. The method of claim 1, wherein identifying the propagation pathlengths of the optical signals comprises determining a phase delay and processing the phase delay with a propagation speed through the tissue for at least one of the optical signals.

5. The method of claim 1,
    wherein detecting presence of the gap between the tissue interface and the tissue comprises comparing at least one of the propagation pathlengths to a propagation pathlength range to determine an invalid application of a tissue interface assembly employed to emit the optical signals for propagation through the tissue.

6. The method of claim 1, wherein the physiological parameter comprises at least one of a total hemoglobin concentration (tHb) parameter, regional oxygen saturation (rSO2) parameter, and arterial oxygen saturation (SpO2) parameter of the blood of the patient.

* * * * *